US008679526B2

(12) United States Patent
Van Den Plas et al.

(10) Patent No.: US 8,679,526 B2
(45) Date of Patent: Mar. 25, 2014

(54) ANTIMICROBIAL PEROXIDASE COMPOSITIONS

(75) Inventors: Dave Van Den Plas, Deurne (BE); Kris De Smet, Mol (BE); Philippe Sollie, Zoersel (BE)

(73) Assignee: Flen Pharma N.V., Edegem (BE)

( * ) Notice: Subject to any disclaimer, the term of this patent is extended or adjusted under 35 U.S.C. 154(b) by 478 days.

(21) Appl. No.: 11/917,330

(22) PCT Filed: Jun. 13, 2006

(86) PCT No.: PCT/BE2006/000067
§ 371 (c)(1),
(2), (4) Date: Mar. 14, 2008

(87) PCT Pub. No.: WO2006/133523
PCT Pub. Date: Dec. 21, 2006

(65) Prior Publication Data
US 2009/0285890 A1    Nov. 19, 2009

Related U.S. Application Data

(60) Provisional application No. 60/689,807, filed on Jun. 13, 2005.

(51) Int. Cl.
| | |
|---|---|
| *A61L 15/22* | (2006.01) |
| *A61L 15/00* | (2006.01) |
| *A61F 13/00* | (2006.01) |
| *A61K 38/44* | (2006.01) |

(52) U.S. Cl.
USPC ........... 424/447; 424/446; 424/445; 424/443; 424/94.4; 424/484; 514/731; 602/48; 602/50

(58) Field of Classification Search
None
See application file for complete search history.

(56) References Cited

U.S. PATENT DOCUMENTS

| | | | |
|---|---|---|---|
| 4,476,108 A | 10/1984 | Kessler et al. | |
| 6,572,843 B1 * | 6/2003 | Sorensen et al. | ................ 424/62 |
| 6,706,279 B1 * | 3/2004 | Hazzi | ........................... 424/443 |
| 2002/0119136 A1 | 8/2002 | Johansen | |

FOREIGN PATENT DOCUMENTS

| | | |
|---|---|---|
| EP | 0 514 417 | 8/1991 |
| WO | WO 92/18683 | 10/1992 |
| WO | WO 01/28600 | 4/2001 |
| WO | WO 02/08377 | 1/2002 |

OTHER PUBLICATIONS

"Anionic iodotyrosine residues are required for iodothyronine synthesis" by de Vijlder et al., Eur. J. Endocrin. 138, 227-31 (1998).*
"Catalase, Peroxidase and Metmyoglobin as Catalysts of Coupled Peroxidatic Reactions" by Keilin et al., Biochem. J. 60, 310-25 (1955).*
"The effect of peroxidase on the bactericidal action of phenols," by Kojima, J. Biochem. 14, 95-109 (1931).*
"Guaiacol as a Dressing for Suppurating Wounds" by Prokhorov, Am. J. Med. Sci. 129, 357 (1905).*
"Solute Diffusion within Hydrogels. Mechanisms and Models" by Amsden, Macromol. 31, 8382-95 (1998).*
International Search Report for PCT/BE2006/000067 Mailed May 23, 2007.
Written Opinion of the International Searching Authority for PCT/BE2006/000067 Mailed May 23, 2007.
de la Brassine et al., "A Novel Method of Comparing the Healing Properties of Two Hydrogels in Chronic Leg Ulcers," *JEADV* 20:131-135 (2006).
Kussendrager, van Hooijdonk, "Lactoperoxidase:Physico-chemical Properties, Occurrence, Mechanism of Action and Applications," *Br. J. Nutr.* 84: (Suppl. 1) S19-S25 (2000).
Fitzgerald et al., "Mode of Antimicrobial Action of Vanillin Against *Escherichia coli, Lactobacillus plantarum*, and *Listeria innocua*," *J. Appl. Microbiol.* 97:104-113 (2004).
Fitzgerald et al., "Structure-Function Analysis of the Vanillin Molecule and its Antifungal Properties," *J. Agric. Food Chem.* 53:1769-1775 (2005).
International Preliminary Report on Patentability (PCT/BE2006/000067), mailed Jan. 3, 2008.
Kootstra et al., "Thyroid peroxidase: kinetics, pH optima and substrate dependency," *Acta Endocrinologica* 129:328-331 (1993).
Examiner's first report on Australian Patent Application No. 2006257730, dated Mar. 17, 2011.
Examiner's report No. 2 on Australian Patent Application No. 2006257730, dated May 26, 2011.

* cited by examiner

*Primary Examiner* — Brandon Fetterolf
*Assistant Examiner* — Theodore R West
(74) *Attorney, Agent, or Firm* — Clark & Elbing LLP

(57) ABSTRACT

The present invention discloses a class of compounds which have an enhancing effect on peroxidase based antimicrobial compositions. The invention relates to pharmaceutical compositions for prolonged topical use comprising enhancing agents such as methoxyphenols and substituted benzylaldehydes. Examples hereof are respectively guaiacol and vanillin.

33 Claims, 8 Drawing Sheets

ANTIMICROBIAL PEROXIDASE COMPOSITIONS

CROSS-REFERENCE TO RELATED APPLICATIONS

This application is the U.S. National Stage of International Application No. PCT/BE2006/000067, filed Jun. 13, 2006, which claims the benefit of U.S. Provisional Application Ser. No. 60/689,807, filed Jun. 13, 2005.

FIELD OF THE INVENTION

The present invention relates to antimicrobial pharmaceutical compositions for topical use and methods for the treatment of wounds and infections using these compositions. More particularly, the invention relates to compositions comprising compounds for enhancing and/or stabilising the activity of antimicrobial peroxidases.

BACKGROUND OF THE INVENTION

Peroxides have been used since long for laundry washing, for bleaching processes in textile and paper industry and also as antimicrobial agents. Peroxidase enzymes are used in these applications to convert hydrogen peroxide into radicals. Certain organic compounds such as p-hydroxycinnamic acid, 2,4-dichlorophenol, p-hydroxybenzene sulphonate, vanillin, p-hydroxybenzoic acid and derivatives have been described in industrial processes for textile bleaching (WO9218683).

The antimicrobial activity of peroxidase based systems depends on the type of electron donor being used. EP514417 demonstrates the effect of iodide and thiocyanate ions on the antimicrobial activity versus bacteria and fungi. This patent also shows an enhancing effect of anti-oxidants on the peroxidase activity. The compositions described to be active against both bacteria and yeast are described to comprise between 0.5 to 200 mg/kg iodide anions, between 2 to 100 mg/kg thiocyanate anions, and between 0.2 to 100 g/kg D-glucose. The weight:weight ratio of iodide:thiocyanate anions in the described compositions is between 0.1:1 to 50:1 and the combined anion weight concentration is at least 5 mg/kg. These compositions further comprise between 10 to 100000 U/kg lactoperoxidase, and contain between 150 to 4000 U/kg glucose oxidase. U.S. Pat. No. 4,476,108 discloses a method for producing bactericidal free radicals in the mouth over a controlled time period by applying a combination of a peroxidase, a peroxide and a source of donor molecules within predetermined concentration levels. The preparation is preferably used in a carrier liquid or paste. The carrier can be water, toothpaste of standard formulation, mouthwash of standard formulation, chewing gum, prophylaxis paste, denture cleaner and oral cleansing gels. More particularly, it discloses anti-microbial compositions for oral application with a short-term activity (less than two minutes) using peroxide, a peroxidase, a donor molecule such as phenylethylamine, tyrosine, tryptophan, benzoic acid, salicylic acid, hydroquinone, dehydrophenylalanine, vanillin and para-aminobenzoic acid. US20020119136 describes a class of dialkoxyphenol compounds (e.g. acetosyringone and alkylsyringates) with an enhancing effect on peroxidases.

Antimicrobial activity as such against fungi and bacteria has been attributed to aromatic flavouring compounds such as syringaldehyde and vanillin [Fitzgerald et al. (2005). *J Agric Food Chem.* 53, 1769-1775; Fitzgerald et al. (2004). *J Appl Microbiol.* 97, 104-113]. The antimicrobial activity is however only observed at high concentrations and after prolonged periods of incubation. Despite the existing variety of peroxidase enhancing compounds there is a need for additional peroxidase enhancing compounds, which are non-toxic, are sufficiently soluble for use in aqueous compositions and have a desired prolonged antimicrobial effect for medical applications such as disinfecting wounds.

SUMMARY OF THE INVENTION

The present invention is based on the surprise finding that a certain group of substituted benzene or phenol molecules, which are water soluble and have a moderate hydrophobicity, are especially suitable for enhancing a peroxidase based antimicrobial pharmaceutical composition for prolonged topical application.

A first aspect of the invention relates to a pharmaceutical composition comprising a peroxide or a peroxide generating system, a peroxidase and an enhancing agent characterised in that the enhancing agent is a benzene molecule substituted with a —OH or a $(CH_2)_n OH$ (n=1, 2, 3 or 4) group and substituted with one alkoxy group (—OR) with a chain length of 1, 2, 3 or 4 carbon atoms. Apart from these two required substituents the benzene molecules can optionally be further substituted with one to 4 substituents each independently selected from the group consisting of an hydroxy group, an aldehyde, a ketone, an acid, a halogen (I, F, Cl, Br), an hydroxyalkyl group with 1, 2, 3 or 4 carbon atoms, a linear or branched alkyl group or a linear or branched alkenyl group with 1, 2, 3 or 4 carbon atoms, wherein said hydroxyalkyl, alkyl or alkenyl groups are further optionally substituted with a halogen, carboxyl, hydroxyl, aldehyde or ketone group. The substituted benzene molecule is preferably soluble in water at a concentration of at least 0.1% (w/v). Further, the substituted benzene molecule can be a lipophilic molecule with a octanol/water partition coefficient X log P between 1 and 4.

Typically, the combination of peroxide or peroxide generating system, peroxidase and enhancing agent optionally combined with one or more halides and/or pseudo-halides is present in the pharmaceutical composition of the invention as active antimicrobial ingredients. According to one embodiment this combination is present as the sole antimicrobial ingredient in the pharmaceutical composition. The present invention describes the combination of peroxide or peroxide generating system, peroxidase and enhancing agent described herein for use as a medicament. More particularly the use of the combination of the present invention is envisaged for the treatment and/or prevention of skin disorders. The pharmaceutical composition is aimed for topical use, more particularly for use on the skin and is for example a hydrophilic wound dressing. In the substituted benzene the —OH or $(CH_2)_n OH$ (n=1, 2, 3 or 4) group and the alkoxy group can be positioned in ortho position. This substituted benzene molecule can be an hydroxyalkyl-alkoxybenzene or an alkoxyphenol or can be an hydroxyalkyl alkoxybenzaldehyde or a hydroxy alkoxybenzaldehyde. The substituted benzene molecule can belong to a group

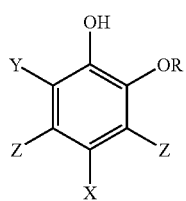

with a general structure represented by formula (I) wherein R is —CH₃ or —CH₂CH₃, wherein X is selected from the group consisting of —H, —CHO and —COCH₃, wherein Y is selected from the group consisting of —H, a halogen and an alkyl group with a chain length of 1, 2, 3 or 4 carbon atoms, and wherein both positions Z are independently selected from the group consisting of —H and an alkyl group with a chain length of 1, 2, 3 or 4 carbon atoms. Said substituted benzene molecule can be a methoxyphenol such as guaicol or can be hydroxymethoxybenzaldehyde such as vanillin. The peroxidase in the composition can be lactoperoxidase and the composition further comprises iodide and/or thiocyanate ions. The peroxidase can be present in a concentration ranging from about 10 to 100 U/kg. The peroxide generating system is in one embodiment an enzymatic peroxide generating system comprising an oxidase enzyme. According to a particular embodiment, the hydrogen peroxide generating enzyme is glucose oxidase. The substituted benzene molecule which acts as enhancing agent can be present in the pharmaceutical composition at a concentration ranging from about 0.01 to 10 mMole/liter. The one or more halides and/or pseudohalides can be present at a concentration of 0.1 to 200 mg/kg.

The pharmaceutical compositions of the present invention comprise one single enhancing agent or comprise a mixture of different enhancing agents in differing ratios.

A particular embodiment of the present invention relates to pharmaceutical compositions as described above, which further comprise one or more halides or pseudo-halides or thiocyanates. More particularly, the compositions comprise a halide. Most particularly, the compositions of the present invention further comprise a halide and not a thiocyanate.

A second aspect of the invention relates to the use of a composition comprising peroxide or a peroxide generating system, a peroxidase and an enhancing agent, for the manufacture of a medicament for the treatment of skin disorders. According to a particular embodiment, the use of a composition comprising as the sole antimicrobial ingredient the combination of a peroxide or a peroxide generating system, a peroxidase, one or more halide or pseudohalide and an enhancing agent. More particularly, the compositions for use in the methods of manufacture of the present invention comprise the combination of a peroxide or a peroxide generating system, a peroxidase an enhancing agent and a halide. Additionally or alternatively, the combinations used in the context of the present invention do not comprise a thiocyanate. One particular embodiment of the invention relates to compositions for use in the methods of manufacture of the present invention comprising the combination of a peroxide or a peroxide generating system, a peroxidase an enhancing agent without a halide or pseudo-halide.

More particularly the topical use of the compositions of the present invention is envisaged in the context of treating and preventing microbial infections, e.g. on the skin. More particularly, the use of the described combination in the manufacture of an antimicrobial composition is envisaged, wherein the enhancing agent is a substituted benzene molecule such as defined in the first aspect of the invention.

A third aspect of the invention relates to a method of treating or preventing a skin disorder, more particularly a microbial infection on the animal or human skin, hair or nails, comprising the step of contacting skin, hair or nails with a composition comprising an effective amount of the combination of the present invention, comprising a peroxide or a peroxide generating system, a peroxidase and an enhancing agent wherein the enhancing agent a is one or more substituted benzene molecule such as defined in the first aspect of the invention. More particularly, the compositions for use in the methods of treatment of the present invention comprise the combination of a peroxide generating system, a peroxidase, one or more halides or pseudo-halides and an enhancing agent. Further embodiments of the methods of treatment and prevention of the present invention relate to the use of compositions comprising the combination of a peroxide or a peroxide generating system, a peroxidase an enhancing agent and a halide. Additionally or alternatively, the combinations used in the context of the present invention do not comprise a thiocyanate. One particular embodiment of the invention relates to compositions for use in the methods of treatment and/or prevention of the present invention comprising the combination of a peroxide or a peroxide generating system, a peroxidase an enhancing agent without a halide or pseudohalide.

More particularly, the invention provides methods of treatment using compositions comprising as a sole antimicrobial ingredient, the combination of peroxide or a peroxide generating system, a peroxidase at least one halide or pseudohalide and an enhancing agent. In a particular embodiment, the skin, hair or nails are contacted with the compositions of the present invention between 2 and 8 hours. According to a further particular embodiment, the skin disorder is a wound or a burn.

A particular embodiment of the invention relates to compositions comprising the combination of peroxide or peroxide generating system, a peroxidase an enhancing agent and optionally one or more pseudo halides specifically formulated for obtaining an antimicrobial effect when applied topically. Typically, the composition is a hydrophilic hydrogel. According to a particular embodiment, the composition is provided as a wound dressing or provided for use on or for the impregnation of structural wound dressings. Typically, the composition is packaged in a sealed container. Thus, the present invention also provides wound dressings comprising a peroxide generating system, a peroxidase an enhancing agent and optionally one or more halides or pseudohalides characterised in that the enhancing agent is a substituted benzene molecule such as defined in the first aspect of the invention. In a particular embodiment, the combination of a peroxide generating system, a peroxidase and an enhancing agent is provided as the sole antimicrobial ingredient therein.

The enhancing agents of the present invention which have a moderate (at least 0.1 mg/ml) or high (at least 1 mg/ml) water solubility are particularly suitable to be formulated in a hydrogel.

Another particular embodiment of the invention relates to a hydrophilic hydrogel wound dressing comprising as active antimicrobial ingredients a peroxide generating system, a peroxidase, guaiacol and optionally one or more halides or pseudohalides.

Another particular embodiment of the invention relates to a hydrophilic hydrogel wound dressing comprising as active antimicrobial ingredients a peroxide generating system, a peroxidase, vanillin and optionally one or more halides or pseudohalides.

Another particular embodiment of the invention relates to the use of a composition comprising as active ingredients peroxide or a peroxide generating system, a peroxidase, vanillin, and optionally one or more halides or pseudohalides for the manufacture of a medicament for topical use with antimicrobial activity.

Another particular embodiment of the invention relates to the use of a composition comprising as active ingredients peroxide or a peroxide generating system, a peroxidase guaiacol, and optionally one or more halides or pseudohalides for the manufacture of a medicament for topical use with antimicrobial activity.

DETAILED DESCRIPTION OF THE INVENTION

Definitions

Figure 1:
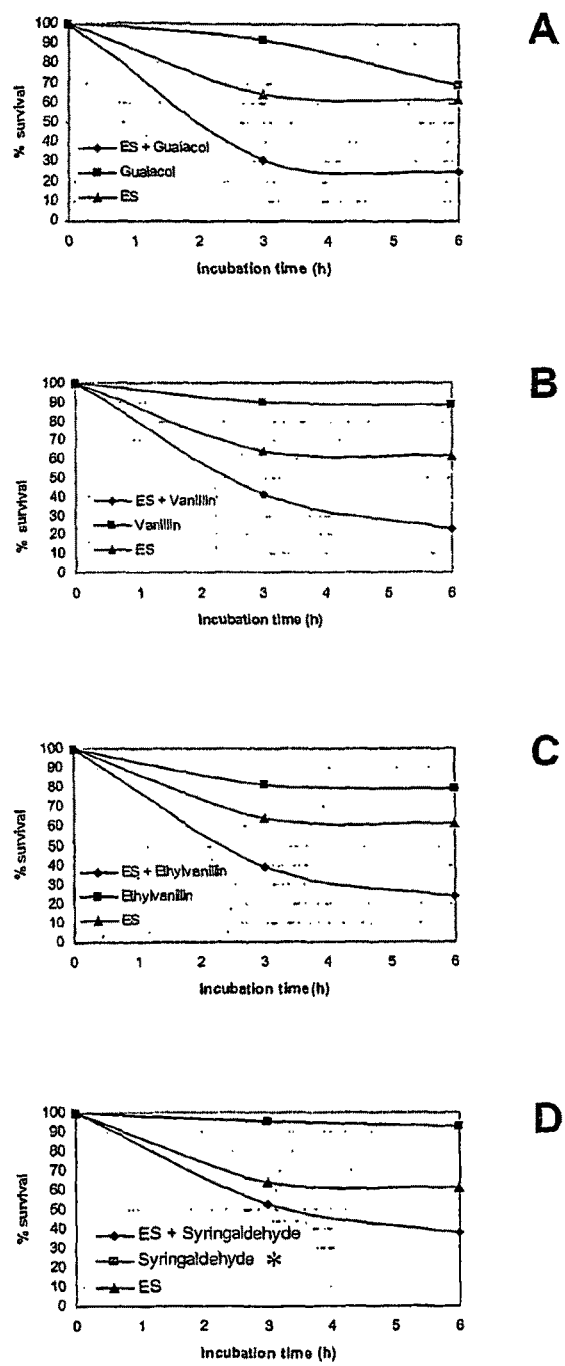
FIG. 1 shows the antibacterial effect on *Staphylococcus aureus* of mixtures of compounds according to one embodiment of the present invention and oxidase/peroxidase A: guaiacol; B: vanillin; C: ethylvanillin; D: Syringaldehyde (comparative example) (♦: enhancing agent and ES (substrate (glucose, KSCN, KI) and enzymes (oxidase/peroxidase)), ■: enhancing agent only; ▲ ES (substrate (glucose, KSCN, KI) and oxidase/peroxidase) only FIG. 2 shows the antibacterial effect of compositions comprising enhancing agents on *S. aureus* according to an embodiment of the present invention. The compositions comprise the enhancing agent indicated, substrate (glucose, KSCN, KI) and enzyme (oxidase/peroxidase) (bars marked with * represent comparative examples) (results are the mean of two independent experiments). 100% depicts enzyme and substrate without substances added.

"Peroxidase" refers to enzymes of E.C. Class 1.11.1.7 and includes lactoperoxidase.

As used herein the reference to 'enzyme/substrate' or 'ES' refers to the combination of the oxidase/peroxidase system and its substrate.

"As used herein a 'halide' refers to an ion of a halogen. A pseudohalide refers to a polyatomic anion resembling the halides in their acid-base and redox chemistry. These include cyanide, thiocyanate, thiosulfate and azide ions.

"Antimicroblal" refers to killing microbes or retarding the growth of microbes. Microbes include bacteria such as gram-negative bacteria (e.g. *Escherichia coli* and *Pseudomonas aeruginosa*), gram-positive bacteria (e.g. *Staphylococcus aureus, Propionibacterium acnes*) and spore-forming bacteria. Microbes include fungi such as moulds (e.g. *Aspergillus niger, Penicillium funiculosum*), yeasts (e.g. *Candida albicans, Saccharomyces cerevisiae, Pityrosporum ovale*) and dermatophytic fungi (e.g. *Trichophyton rubrum*). The term antimicrobial thus comprises the terms "bactericidal", "bacteriostatic", "fungicidal" and "fungistatic". Microbes may also include microalgae such as *Chlorella* spp. and *Spyrogyra* spp. and viruses such as Herpes virus, Picornavirus, Varicella and warts.

"Parasite" refers to higher evolved organisms such as insects (e.g. louse and ticks), nematodes and the like which infect skin, nails, hair and lungs, rectum, vagina eye, ear, and nose.

The "hydrophobicity" is expressed as the partition coefficient of a compound in an octanol/water two component system (X log P). The higher the value of X log P, the more hydrophobic the compound. X log P values can be found or predicted on several websites.

"Topical" in the present application refers to both external human or animal (e.g. skin, nails or hair), and internal (e.g. lungs, rectum, vagina, eye, ear, and nose) tissues covering the body.

The term "skin disorder" as used herein generally refers to any aberrant condition of the skin, including but not limited to microbial infections.

The present invention relates to the use of a class of compounds, referred to herein as "enhancing agents" to enhance peroxidase based anti-microbial activity, more particularly in the context of therapeutic and prophylactic compositions. The compounds are benzene- or phenol-substituted compounds which are water-soluble compounds, and have a moderate hydrophobicity. The water solubility of the compounds of the invention is at least 0.1 mg/ml, more preferably at least 1 mg/ml. The hydrophobicity of the compounds of the invention (X log P) is between 1 and 4, more preferably between 1 and 2.

In the broadest sense, the enhancing agents envisaged in the context of the present invention are benzene molecules which are substituted at one, two, three or four positions with a substituent selected from the group consisting of a hydroxyl group and a hydroxyalkyl group or a halogenated hydroxyalkyl group with 1, 2, 3 or 4 carbon atoms. The hydroxyalkyl groups are represented by the general formula —$(CH_2)_n$OH (n=1, 2, 3 or 4). In such a hydroxyalkyl group the —OH can be terminal (e.g. —$CH_2$—$CH_2$—$CH_2$—OH) but can also be located on another carbon atom of the alkyl chain (e.g, —$CH_2$—CHOH—$CH_2$—$CH_3$ or —$CH_2$—$CH_2$—CHOH—$CH_3$).

The compounds are further substituted at only one position with an alkoxy group or halogenated alkoxy group with a chain length of 1, 2, 3 or 4 carbon atoms. Apart from these two required substituents the molecules can optionally be further substituted with one or more substituents each independently selected from the group consisting of a hydroxy group, an aldehyde, a keton, an acid and a halogen (I, F, Cl, Br), a hydroxyalkyl group with 1, 2, 3 or 4 carbon atoms, a linear or branched alkyl group or a linear or branched alkenyl groups with 1, 2, 3 or 4 carbon atoms, wherein the hydroxyalkyl, alkyl or alkenyl groups are further optionally substituted with a halogen, carboxyl, hydroxyl, aldehyde or ketone group. Other possible substituents are sulphur, nitro and nitroso groups. One particular embodiment of the invention relates to subgroups of the compounds of the present invention wherein, with respect to an —OH substituent on the benzene ring, a conjugated side chain (e.g. —C=O, —C≡C) or an electrophilic group is present (such as —OH, —OR, halogen) in either ortho position or para position, but not in meta position. When more than one —OH substituent is present, the beneficial effect of said electrophilic group at the ortho or para position towards the —OH group, is diminished or annihilated by position of the electrophilic group in meta positions to another —OH-group. According to an embodiment, the required —OH or —$(CH_2)_n$OH (n=1, 2, 3 or 4) group and the alkoxy group are in ortho position. According to certain embodiments the substituted benzene molecule is substituted at two positions and belongs to the class of hydroxyalkyl-alkoxybenzenes or alkoxyphenols.

According to certain embodiments the substituted benzene molecule is substituted at three positions and belongs to the class of hydroxyalkyl alkoxybenzaldehydes or hydroxy alkoxybenzaldehydes.

A subclass of the enhancing agents envisaged in the context of the present invention are substituted phenol molecules with a general structure represented by formula (I)

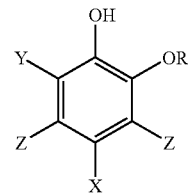

(I)

Wherein R is —$CH_3$ or —$CH_2CH_3$, wherein X is selected from the group consisting of —H, —CHO and —$COCH_3$, —COOH wherein Y is selected from the group consisting of —H, a halogen and an alkyl group or halogenated alkyl group with a chain length of 1, 2, 3 or 4 carbon atoms, and wherein both positions Z are independently selected from the group consisting of H and an alkyl group or halogenated alkyl group with a chain length of 1, 2, 3, or 4 carbon atoms.

Particular embodiments of enhancing agents envisioned in the context of the present invention are hydroxymethoxyphenols (such as guaiacol (2-methoxyphenol), 2-ethoxyphenol and 2-propoxyphenol) and hydroxymethoxybenzaldehydes (such as vanillin (4-hydroxyl-3-methoxy-benzaldehyde), ethylvanillin (4-hydroxyl-3-ethoxybenzaldehyde) and 4-hydroxyl-3-prophoxybenzaldehyde), bromovanillin and nitrovanillin.

According to specific embodiments, the enhancing agents envisaged in the context of the present invention are non-toxic compounds and/or compounds which are recognised as GRAS compounds (Generally Accepted As Save). According to other specific embodiments the compounds of the invention are compounds known as flavouring and perfuming agents.

A number of enhancing agents envisaged in the context of the present invention is listed in Table 1.

TABLE 1

| compounds of the present invention | | |
|---|---|---|
| name | Solubility in water (g/liter) | XLogP * |
| o-vanillin (2-hydroxy-3-methoxy-benzaldehyde) | 0.50 | 1.84 |
| Vanillin (4-hydroxy-3-methoxy-benzaldehyde) | 11 | 1.24 |
| Vanillic acid (4-hydroxy-3-methoxy-benzoic acid) | 0.15 | 1.12 |
| 5-hydroxy-3-methoxy-benzaldehyde | | |
| Isovanilline (3-hydroxy-4-methoxy-benzaldehyde) | 11 | 1.24 |
| Quantrovanil (3-ethoxy-4-hydroxy-benzaldehyde) | 0.28 | 1.65 |
| Apocynin (1-(4-hydroxy-3-methoxy-phenyl)ethanone) | 0.5 | 1.41 |
| (2-methoxybenzene-1,4-diol) | | |
| (4-methoxybenzene-1,2-diol) | | |
| Guaiacol (2-methoxyphenol) | 18.7 | 1.55 |
| m-Guaiacol (3-methoxyphenol) | 0.5 | 1.55 |
| bromovanillin (3-bromo-4-hydroxy-5-methoxy-benzaldehyde) | | 2.03 |
| Chlorovanillin (3-chloro-4-hydroxy-5-methoxy-benzaldehyde) | | 1.86 |
| Leucobasal (4-methoxyphenol) | 40 | |

TABLE 1-continued compounds of the present invention

| name | Solubility in water (g/liter) | XLogP * |
|---|---|---|
| Ethylvanillin (3-ethoxy-4-hydroxy-benzaldehyde) | 2.8 | 1.65 |
| Guaiethol (2-ethoxyphenol) | 3.1 | 1.96 |
| Isoethylvanillin (4-ethoxy-3-hydroxy-benzaldehyde) | | |
| 2-propoxyphenol | | 2.41 |
| 2-Methoxyresorcinol (2-methoxybenzene-1,3-diol) | | 1.17 |
| 3-Methoxypyrocatechol (3-methoxybenzene-1,2-diol) | | 1.17 |
| Methoxyhydroquinone (2-methoxybenzene-1,4-diol) 4-methoxybenzene-1,2-diol | 33 | 1.17 |

* XlogP values were taken from the PubChem website (http://pubchem.ncbi.nlm.nih.gov/)
* solubility data were taken from nlm-SIS http://chem.sis.nlm.nih.gov/chemidplus/

Another aspect of the present invention provides pharmaceutical compositions comprising one or more of the enhancing agents described above and further comprising a peroxidase, a peroxide or a peroxide generating system, and one or more pharmaceutically acceptable carriers. The compositions optionally comprise one or more halides or pseudohalides.

The invention is based on the observation that the activity of peroxidase-based antimicrobial activity is increased in the presence of one or more of the enhancing agents described herein.

According to the present invention, compositions are provided having peroxide-based antimicrobial activity. This activity can be antibacterial, antifungal and/or directed against any other micro-organisms.

According to a particular embodiment, the peroxidase-based antimicrobial activity is generated by one or more peroxidase enzymes capable of generating ions with antimicrobial activity.

Suitable peroxide-based antimicrobial activity used in the context of the present invention are peroxidase enzymes capable of oxidizing halide and/or pseudohalides (such as isothiocyanate) ions. Examples of peroxidase enzymes suitable in the context of the present invention are peroxidase capable of oxidising one or more of a chloride ion, iodide ion, bromide or a thiocyanate ion to an antimicrobial hypochlorite, hypoiodite, hypobromite or hypothiocyanite ion, respectively.

According, to a particular embodiment a haloperoxidase is used, i.e. en enzyme capable of oxidizing halides to hypohalite.

Particular examples of peroxidase enzymes suitable in the context of the present invention are e.g. myeloperoxidase, lactoperoxidase and chloroperoxidase, salivary peroxidase and eosinophil peroxidase.

According to a further embodiment, the peroxidase present in the compositions of the invention is derived from plants (e.g. horseradish or soybean peroxidase) or from micro-organisms such as fungi or bacteria.

According to a particular embodiment, the peroxidase-based antimicrobial activity is generated by lactoperoxidase. Lactoperoxidase is capable of converting different substrates including but not limited to iodide and thiocyanate which act as electron donors.

According to one embodiment, the compositions of the present invention comprise a peroxidase and one or more halides or pseudo-halides (such as thiocyanate) ions as electron donor for the peroxidase. Suitable halides are, for example, ionic iodides under the form of water-soluble iodide salts such as an alkaline metal iodide salt, e.g. potassium iodide (KI), sodium iodide (NaI), or lithium iodide, ammonium iodide, calcium iodide. Typical examples are sodium iodide and potassium iodide.

Suitable sources of the thiocyanate ion (SCN$^-$) include sodium thiocyanate, potassium thiocyanate, ammonium thiocyanate, and other thiocyanate salts. Typical examples are sodium thiocyanate and potassium thiocyanate.

According to a particular embodiment the compositions of the present invention comprise lactoperoxidase and both a thiocyanate and a halide as electron donors.

According to yet a further embodiment, the compositions of the present invention comprise a peroxidase as described above and only (one or more) halide as electron donor for the peroxidase. The present invention demonstrates that compositions comprising a combination of a peroxide or a peroxide-generating system, a peroxidase, an enhancing agent and a (one or more) halide are effective antimicrobial compositions. This not only allows a reduction of the number of active ingredients but makes it possible to avoid the addition of thiocyanate ion-generating compounds which may be toxic. Thus, according to a particular embodiment, the compositions of the present invention do not comprise a thiocyanate or other pseudo-halides.

As detailed above, the compositions of the present invention comprise either a peroxide per se or a peroxide generating system. Typically, the peroxide-generating system comprises a peroxide generating enzyme and a substrate. According to one embodiment, the peroxide generating enzyme is an oxidoreductase enzyme. Suitable oxidoreductases are glucose oxidase, galactose oxidase, glycollate oxidase, lactate oxidase, L-gulunolactone oxidase, L-2-hydroxyacid oxidase, aldehyde oxidase, xanthine oxidase, D-aspartate oxidase, L-amino acid oxidase, D-amino acid oxidase, monoamine oxidase, pyridoxaminephosphate oxidase, diamine oxidase, and sulphite oxidase.

Suitable substrates for use in the peroxide generating system according to the present invention include the natural substrates of the enzymes listed above, as well as other substrates, which allow the generation of peroxide. Beta-D-glucose is a specific substrate for glucose oxidase. Other suitable substrates include, but are not limited to D-glucose, D-galactose, L-sorbose, ethanol, tyramine, 1,4-diaminobutane, 2-aminophenol, glycollate, L-lactate, 2-deoxy-D-glucose, L-gulunolactone, L-galaconolactone, D-mannonolactone, L-2-hydroxyisocaproate, acetaldehyde, butyraldehyde, xanthine, D-aspatate, D-glutamate, L-amino acids and D-amino acids.

Typically, glucose and glucose oxidase are used as hydrogen peroxide generating system.

As an alternative, the peroxide generating system is non-enzymatic and the hydrogen peroxide is generated in alternative ways, e.g. by molecules which naturally degrade generating peroxide, such as perborate or percarbonate salts, more particularly sodium percarbonate or sodium perborate.

The components of the combinations of the present invention are provided in concentrations which allow effective antimicrobial activity.

Typical pharmaceutically effective concentrations of peroxidase are between 10 to 100.000 U/kg, 100 to 25000 U/kg, 250 to 10000 U/kg, or 500 to 7000 U/kg lactoperoxidase. Using the enhancing agents of the invention, peroxidase concentrations used can be in the range between 5 to 50 Units/kg, 10 to 100 U/kg, 20 to 250 U/kg, 50 to 500 Units/kg, 100 to 1000 U/kg, 200 to 2500 U/kg. Typical pharmaceutically effective concentrations of glucose oxidase are between 150 to 4000 U/kg, 200 to 3000 U/kg, 300 to 2500 U/kg glucose oxidase.

Where present, the concentration of iodide anions can be 1 to 200 mg/kg, 2 to 150 mg/kg, 5 to 75 mg/kg. The concentration of halide or pseudohalide anions (such as thiocyanate) can be 1 to 100 mg/kg, 2 to 75 mg/kg or 5 to 50 mg/kg. Where applicable, the weight:weight ratio of iodide:thiocyanate anions can be 0.2:1 to 20:1, 0.5:1 to 15:1, or 1:1 to 5:1. The combined anion weight concentration can be 5 to 200 mg/kg, or 10 to 150 mg/kg.

The enhancing agents are present in the compositions of the present invention at a concentration between 1 to 10 mMole/liter, 2-5 mMole/liter, 2 to 10, 1 to 25 mMole/liter, 5 to 50 mMole/liter or 5 to 100 mMole/liter. Effective antimicrobial effects against bacteria are obtained with 0.01, 0.1, 1, 0.5, 1, 2.5, 5, 10, 50 and 100 mMole/liter. Effective antimicrobial effects against fungi are obtained with 0.01, 0.1, 1, 0.5, 1, 2.5, 5, 10, 50 and 100 mMole/liter. Enhancing agents of the present invention are present in the compositions of the present invention at a concentration between 1 to 100 mg/10 g (e.g. 1 to 5 mg/100 g, 1 to 10 mg/100 g, 5 to 20 mg/100 g, 10 to 50 mg/100 g, 20 to 50 mg/100 g, 25 to 75 mg/100 g or 50 to 100 mg/100 g).

In particular embodiments the pharmaceutical compositions comprise between 0.25 to 5% glucose, between 0.01 and 0.1% iodium salt such as KI, between 0.5 and 5 U/ml glucose oxidase, between 0.5 and 5 U/ml peroxidase and between 10 and 400 µM of an enhancing agent or a mixture of enhancing agent such as guaiacol and/or vanillin.

According to one embodiment of the invention, the compositions of the present invention comprise both a peroxidase enzyme and an electron donor for the peroxidase. Typically, when lactoperoxidase is used, iodide and/or thiocyanate ions are added as donors for the lactoperoxidase enzyme.

According to an alternative embodiment the enhancing agents of the present invention partially or completely replaces the donor molecule. This has as an additional advantage that toxic compounds such as thiocyanates can fully or partially be replaced by less toxic or non-toxic compounds.

Thus, in a particular embodiment, the antimicrobial active compound in the pharmaceutical compositions of the present invention consist of a peroxide or a peroxide generating system, a lactoperoxidase, a halide and an enhancing agent. In a further particular embodiment, the antimicrobial active compound in the pharmaceutical compositions of the present invention consist of a peroxide or a peroxide generating system, a lactoperoxidase, iodide anions and enhancing agent. Typically, the enhancing agent of the present invention is vanillin or guaiacol.

The enhancing agents of the present invention, when present in the pharmaceutical composition, have the advantage that the antimicrobial activity is maintained over a much longer period than without these compounds, with as a result that the ointment, gel, dressing or the like needs to be less frequently replaced, which reduces the discomfort of the patient being treated.

Accordingly, the present invention provides for pharmaceutical compositions which are suitable for prolonged use on the skin.

The compositions of the present invention optionally further comprise one or more pharmaceutical carriers. The following preparations are examples of aqueous or hydrophilic pharmaceutical carriers which are suitable for dissolving the enzymes and enhancing agents of the present invention. Products can be prepared sterile or non-sterile. The preparations are either aqueous or hydrophilic, i.e. preparations will upon contact with an aqueous medium readily either dissolve in the aqueous medium either readily liberate the drug to the aqueous medium.

Aerosols are suspensions of fine solid or liquid particles in a gas. They are used to apply drugs to the respiratory tract and skin. Sprays are atomised in devices known as atomisers or nebulisers. The patient introduces the solution and by applying pressure to a bulb ejects the product as a mist suspended in air. An alternative, more modern technique is to pack the drug in a pressured container. The drug is dissolved in a solvent or suspended in the propellant (liquefied gas). Pressurized containers provide good protection from oxidation, light and, where necessary, as with sterile dermatological products, micro-organisms (see also insufflations).

Collodions are fluid preparation for external use, They are applied with a brush or rod. The vehicle is volatile and evaporates on application to the skin (ether and alcohol), leaving a flexible, protective film covering the site. The film producing ingredient is generally pyroxylin (nitrocellulose) and the substance giving flexibility castor oil.

Creams are semi-solid emulsions for external use. In an aqueous cream the oil, in a very fine state of subdivision, is dispersed in the aqueous phase, in oily creams the aqueous phase, in a very fine state of subdivision, is dispersed in the oily phase. The cream is stabilised by the inclusion of an emulsifying agent, by the inclusion of gels, gelling agents or other means to increase the viscosity.

Dusting powders are free-flowing, very fine powders for external use.

Emulsions are liquid dispersions of an aqueous phase distributed in an oily phase, or of an oily phase distributed in an aqueous phase. The dispersion is stabilised by the inclusion of an emulsifying agent.

(Hydro)gels are aqueous colloidal suspensions of a colloid in which particles are in the external or dispersion phase and water is in the internal or dispersed phase. Different components suitable for the manufacture of pharmaceutically acceptable hydrogels are known to the skilled person. Hydrogels are generally used for retaining or absorbing moisture or water. Suitable hydrogels in the context of the present invention are prepared with hydrocolloids such as alginates and polyacrylates (eg carbopol) and cellulose and derivatives thereof such as carboxymethyl cellulose (CMC). Other suitable hydrocolloids are aluminium hydroxide, siliciumdioxide or silicium acid, starch, glycogen, gelatin, pectin, chitosan, chitin, gum Arabic, locust bean gum, karaya gum, gum tragacanth, ghatti gum, agar-agar, carrageenans, carob gum, guar gum, xanthan gum, glyceryl polymethacrylate. A hydrogel can be used as such. Hydrogels for use in the context of the present invention can be formulated with different concentrations of colloid depending on the desired consistency.

Glycerins are solutions of the drug in glycerol with or without the addition of water.

Insufflations are medicated dusting powders that are blown by an insufflator (a device similar to an atomizer or pressurised atomizer).

Jellies (Gels) are transparent or translucent, non-greasy, semisolid preparations. The gelling agent may be gelatin, or a carbohydrate or other polymer known as gelling agent.

Liniments are fluid, semi-fluid or, occasionally, semi-solid preparations intended for application to the skin. They may be alcoholic or oily solutions of emulsions. Most are massaged into the skin but some are applied on a dressing or with a brush.

Lotions are fluid preparations for external application without friction. They are either dabbed on the skin or applied on a suitable dressing and covered with waterproof material to reduce evaporation.

Mixtures are the most common form of liquid preparation. The vehicle is usually aqueous and the drug may be in suspension or in solution.

Ointments are semi-solid greasy preparations. The base is usually anhydrous and contains the medicament in solution or suspension.

Oxymels are preparations in which the vehicle is a mixture of an acid and honey.

Paints are liquids for application to the skin or mucosae, usually with a soft brush. Skin paints often have a volatile solvent that evaporates quickly to leave a dry or resinous film of medicament. Paints can be made viscous by the addition of glycerin, which is sticky, adheres to the affected site and prolongs the action of the drug.

Pastes are semisolid preparations for external applications that differ from similar products in containing a high proportion of finely divided powdered medicaments. The base may be anhydrous (liquid or soft paraffin) or water-soluble (glycerol or a mucilage). Their stiffness makes them useful as protective coatings.

Solutions are used for many purposes. For some of these sterility is necessary.

Sprays are preparations of drugs in aqueous, alcoholic or glycerin containing media. They are applied to the mucosae or (broken) skin with an atomiser or nebuliser.

The present invention also relates to a method of treating or preventing a topical microbial infection of an animal or human comprising the step of applying topically to said animal or human a pharmaceutical composition comprising the combination of the present invention comprising a peroxide or a peroxide generating system a peroxidase enzyme and an enhancing agent. The pharmaceutical compositions used in the methods of the invention optionally further comprise one or more halides and/or pseudohalides. The method of treatment can thus be used in veterinary and human medical treatment.

According to one embodiment, the methods of the invention are performed on intact nails, hair and/or skin. Additionally or alternatively, the methods comprise application on wounds, burns, and those parts of the skin, nails or hair which are infected with parasites. Examples of infections envisaged to be treated in the context of the present invention include, but are not limited to folliculitis, furuncolosis, carbuncle, impetigo, erysipelas, Lyme disease, Herpes, Zona, pytoriasis versicolor, Intertrigo, and lice, flea and scabies infections.

The treatment with the composition of the present invention optionally comprise maintaining the composition in contact with the body for a period of several hours (e.g. 2, 4, 6 or 8 hours), whereafter the composition is optionally reapplied. It is an advantage of the present invention that the prolonged activity of the peroxidase enzyme in combination with the enhancing agents makes it possible to refresh to the composition less frequently than when a composition without said compounds would be used. This is particularly of interest for painful wounds such as burns.

Accordingly, the present invention also relates to the use of the enhancing agents of the present invention for the manufacture of a medicament or device for topical application for the treatment or prevention of topical microbial or parasitic infections.

The pharmaceutical compositions for topical use can be formulated as a skin cream, lotion, foundation, ointment, lotion, suspension (oil-in-water and water-in-oil), patches, dressing or gel. Such compositions include deodorants in the form of roll-on or stick formulations, anti-acne preparations e.g. in the form of lotions or creams, impregnated materials such as wound dressings, pharmaceuticals for wound irrigants and burn treatments. Ear drops, nose drops, inhalation, vaginal, rectal solutions or emulsions. As the invention aims a prolonged antimicrobial effect, application in the oral cavity is not envisaged, because the pharmaceutical composition will be removed via swallowing within a period of a few minutes.

The examples provided below are intended to illustrate the invention but in no way are intended to limit the invention to the embodiments described therein.

EXAMPLES

Example 1

Antibacterial Activity on *S. aureus* of Oxidase/Peroxidase with Enhancing Agents Bacterial cells (*S. aureus*) were plated on Trypticase Soybean Agar plates (Becton Dickinson) and incubated overnight at 37° C. Cells were recovered from plates and mixed with NaCl-peptone broth buffer (Merck). The amount of medium is adjusted to give a bacterial suspension with a cell density of $OD_{600}$=0.25 for bacteria.

For the examples described in the following examples, a fresh dilution of 0.25% (v/v) enzyme-substrate (Biovert™) stock solutions were prepared for each independent test. The Biovert™ enzyme stock solution contains 1527 U/ml lactoperoxidase; 2016 U/ml glucose oxidase; the Biovert™ substrate stock solution comprises: 55% (w/v) glucose, 0.51% (w/v) KSCN, 0.73% (w/v) KI.

In order to assess the synergistic action of the enhancing agent on the enzyme-substrate enhancing agent, the concentration of enzyme-substrate was adjusted to obtain conditions wherein the oxidase/peroxidase in a hydrogel performs limited but measurable antibacterial activity. The above mentioned (0.25% (v/v)) solution has accordingly been further diluted to 0.017% (v/v).

A 0.33% (w/v) Na-alginaat (Kelset), 0.66% (v/v) PEG400 gel solution was prepared in water, autoclaved and subsequently cooled to room temperature.

For the antibacterial assay the following components are mixed: 100 µl of bacterial cell suspension, 100 µl enzyme-substrate master solution (0.25%), 1 g (=1 ml) gel solution, 0.1-1 mg enhancing agent, 300 µl milliQ water. Final concentrations of the enzyme/substrate in the reaction mixture are 0.015 U/ml glucose oxidase, 0.011 U/ml lactoperoxidase, 0.00007% (w/v) potassium thiocyanate, 0.0001% (w/v) potassium iodide, 0.0076% glucose, and 0.066-0.66 mg/ml enhancing agent.

As shown in FIG. 1, vanillin, ethylvanillin and guaiacol markedly enhanced the bactericidal capacity when mixed with the enzyme-substrate solution, whereas the separate systems only moderately affected cell survival.

Figure 2:
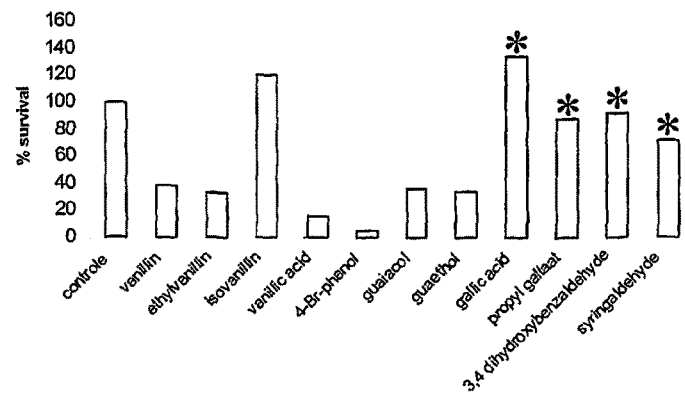

FIG. 2 indicates that, when a conjugated or electrophilic side chain is present at the meta position relative to a hydroxylgroup (e.g. isovanillin and comparative examples 3,4 dihydroxybenzaldehyde, gallic acid and propyl gallate), the antibacterial activity is less pronounced.

Compounds with a low solubility in water or in hydrophilic media (e.g. syringaldehyde) could not be properly dispersed or dissolved and are not suitable in the present experimental setting or for use in a hydrophilic pharmaceutical composition such as a hydrogel.

Furthermore, substances with an X log P below 0 such as tyrosine (X log P=−1.87) or 5-hydroxy-tryptophane (X log P=−1.80) did not show an enhancing activity on glucose/peroxidase antibacterial activity in the present experimental setting.

Pyrocatechol (1,2 dihydroxyphenol) could not be used as a comparative example in view of its toxicity.

Example 2

Antioxidant Properties of Enhancing Agents of the Invention a) DPPH-Radical Bleaching Assay.

DPPH (1,1-DiPhenyl-2-PicrylHydrazyl) is a cell-permeable, stable free radical that acts as a hydrogen radical scavenger, and is used as a screening tool for detecting free radical scavenging activity of antioxidants. When a radical solution is brought into contact with an antioxidant, the radical-molecule is reduced and thereby looses its characteristic purple colour. This "bleaching" can be monitored by spectrophotometric analysis.

A DPPH-radical solution (15 mg/ml) was prepared freshly in 1-octanol (Sigma) and 900 µl aliquots were transferred to 2 ml spectrophotometer cuvettes. 100 µl of 50 mMole/liter solutions of enhancing agents (dissolved in 1-octanol) were added to the solution (final concentration of the enhancing agents is 5 mMole/liter). Spectrophotometric analysis of the samples was carried out within 5 minutes, in order to prevent quenching caused by free (e.g. air born) radicals.

b) Beta-Carotene Assay

In this assay, the antioxidant activity of a component is assessed by its ability to prevent bleaching of a beta-carotene solution by radicals formed upon illumination.

A beta-carotene solution (20 mg/ml) was prepared freshly in 1-octanol (Sigma) and 900 µl aliquots were transferred to 2 ml spectrophotometer cuvettes. 100 µl of 50 mMole/liter solutions of enhancing agents of the invention (dissolved in 1-octanol) were added to the solution (final concentration of the enhancing agents is 5 mMole/liter). The solutions were illuminated for up to 5 hours and spectrophotometric analysis was carried out at indicated time points.

Figure 3:
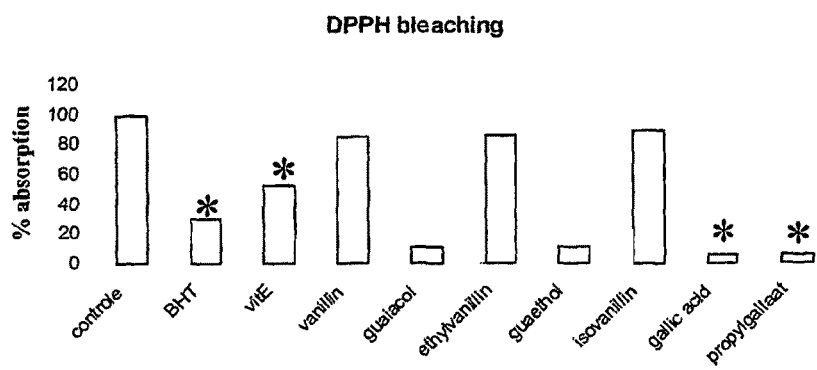
FIG. 3 shows DPPH-radical bleaching of compounds according to an embodiment of the present invention (comparative examples are indicated with *). Results are the mean of two Independent experiments.

FIG. 3 shows that the established antioxidants performed well in the beta carotene bleaching assay. Of the enhancing agents of the present invention, guaiacol and guaethol were very effective molecules, whereas vanillin and ethylvanillin performed poorly as antioxidants in this test.

Figure 4:
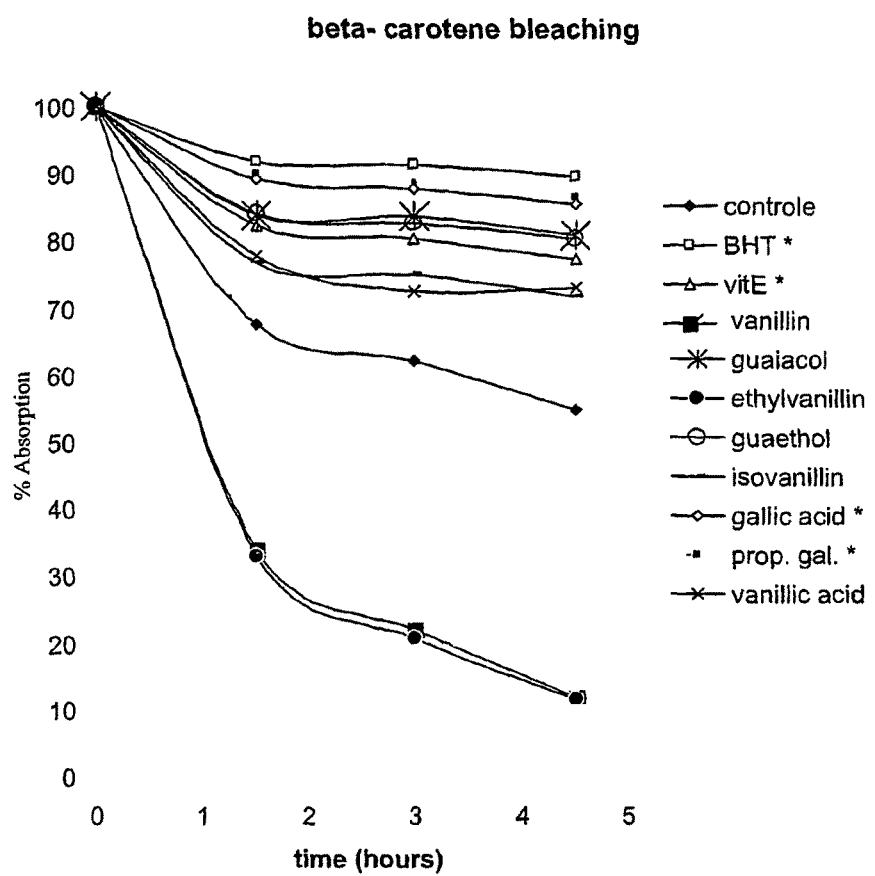
FIG. 4 shows beta-carotene bleaching of compounds according to an embodiment of the present invention (comparative examples are indicated with *) (Results are the mean of two independent experiments).

The data in FIG. 4 confirm the results observed in FIG. 3. They show that the established antioxidants di-tert-butylated hydroxytoluene (BHT) and vitamin E were less potent reducers than gallic acid and propyl gallate. Vanillin and ethylvanillin performed poorly, whereas guaiacol and guaethol were nearly as efficient as gallic acid and propyl gallate.

Comparison of the results (see table 2) of the anti-oxidant assay and of the antimicrobial tests shows that the antioxidant properties of a molecule are not correlated with the enhancing antibacterial effect in a glucose/peroxidase assay.

TABLE 2 anti-oxidant and effect on antimicrobial effect of enhancing agents

| | Antioxidant properties | | |
| --- | --- | --- | --- |
| | Beta-carotene assay | DPPH assay | Enhancing effect on oxidase/peroxidase assay |
| BHT | +++ | ++ | + |
| Vitamin E * | + | + | − |
| Vanillin | − | − | + |
| Guaiacol | ++ | +++ | + |
| Ethylvanillin | − | − | + |
| Guaethol | ++ | +++ | + |
| Isovanillin | ± | − | − |
| Gallic acid * | +++ | +++ | + |
| Propylgallate * | +++ | +++ | ± |
| Vanillic acid | ± | ND | + |

* Comparative examples,
ND: not determined;
+ to +++: moderate to very strong enhancing effect;
±: neglectable effect;
−: no effect Example 3

Antibacterial Activity on MRSA *S. aureus*. of Oxidase/Peroxidase with Enhancing Agents The effect of vanillin and guaiacol on the peroxidase/oxidase activity was assayed on MRSA (methicillin resistant *S. aureus*) bacteria using growth conditions and assay conditions as described in example 1.

Figure 5:
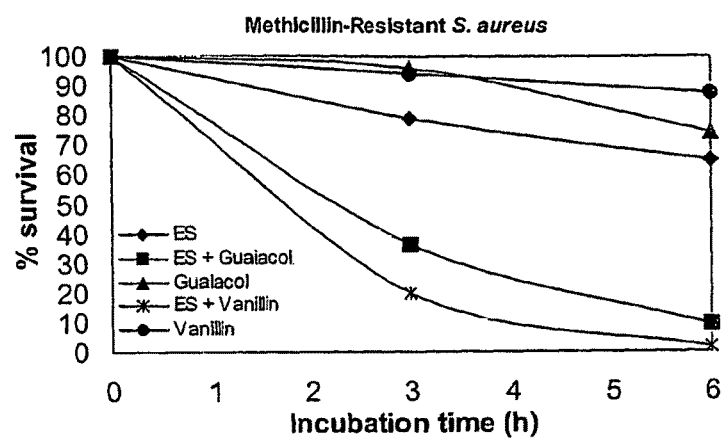
FIG. 5 shows the antibacterial effect on Methicillin-Resistant *Staphylococcus aureus* (MRSA) bacteria of compositions according to an embodiment of the present invention comprising ES (=enzyme (oxidase/peroxidase)+substrate (glucose), KSCN, KI), ES+enhancing agent, or enhancing agent alone.

FIG. 5 shows that both vanillin and guaiacol have an enhancing effect on the peroxidase/oxidase activity, while these compounds alone have a limited effect.

Figure 6:
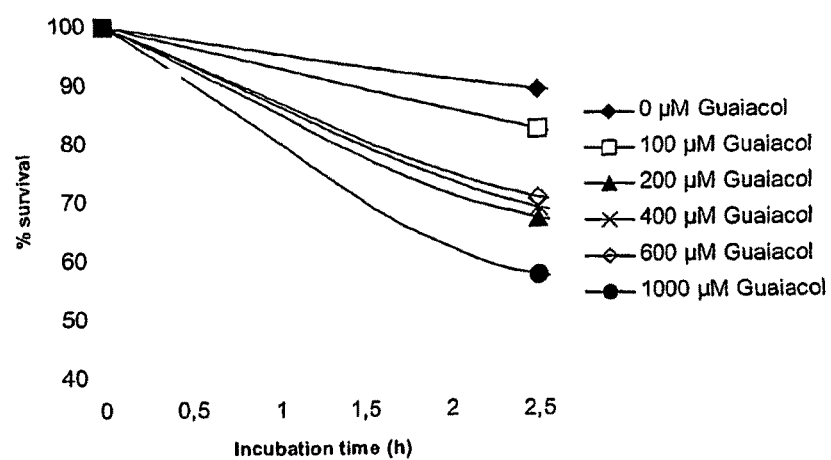
FIG. 6 shows the antibacterial effect of different concentrations of compositions comprising enzymes, substrate and different concentrations of guaiacol on Methicillin-Resistant *Staphylococcus aureus* (MRSA) bacteria.

FIG. 6 shows that, under these conditions guaiacol has a significant enhancing effect on peroxidase/oxidase activity.

Example 4

Antibacterial Activity on *E. coli* of Enhancing Agents and Oxidase/Peroxidase

Figure 7:
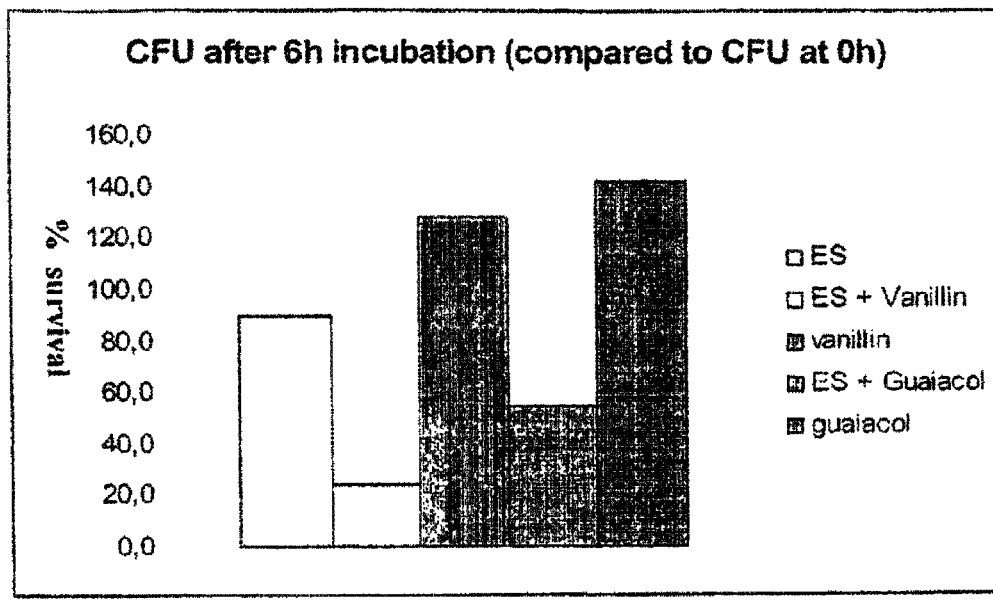
FIG. 7 shows the antibacterial effect on *Escherichia coli* (Gram negative bacteria) of mixtures of compositions according to an embodiment of the present invention comprising ES (=enzyme (oxidase/peroxidase)+substrate (glucose), KSCN, KI) alone, ES+enhancing agent or enhancing agent alone after 6 hours of incubation.

Experiments using the conditions described in Example 1 and 2 were performed with Gram-negative bacteria (*E. coli*). FIG. 7 shows that both guaiacol and vanillin in combination with the enzyme-substrate are more effective than enzyme-substrate alone.

Example 5

Antibacterial Effect on Bacteria and Fungi of Oxidase/Peroxidase with Enhancing Agents a) MRSA (Methicillin-Resistant *Staphylococcus aureus*)

Figure 8:
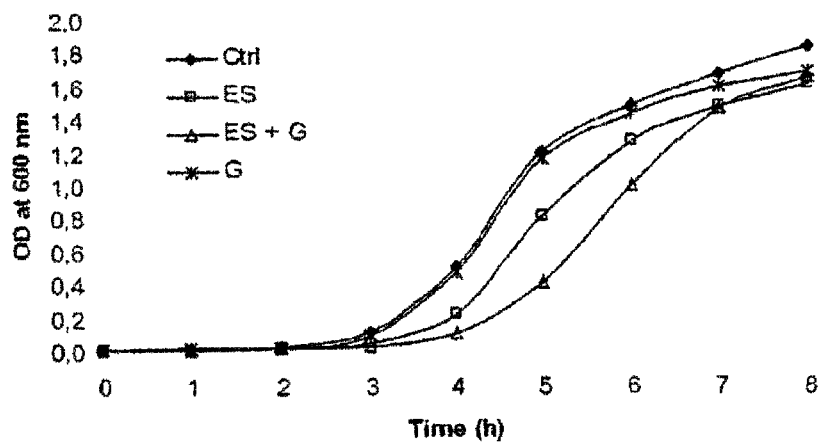
FIG. 8 shows the growth retardation of MRSA bacteria in the presence of ES (enzyme, substrate+halide), guaiacol (G) and enzyme, substrate+halide with guaiacol (ES+G). Growth medium without oxidase/peroxidase are used as reference (Ctrl) according to an embodiment of the present invention.

A bacterial cell culture (A600=0.02) was grown in Tryptic Soy (TS) broth (Difco™, Becton Dickinson) in the presence of a 0.08% dilution (suboptimal concentration) of the enzyme/substrate system described in example 1. The addition of guaiacol shows that an additional suppression of the bacterial growth is obtained. (see FIG. 8). It is observed that this effect is maintained for a significant time period.

b) *Candida albicans*

Figure 9:
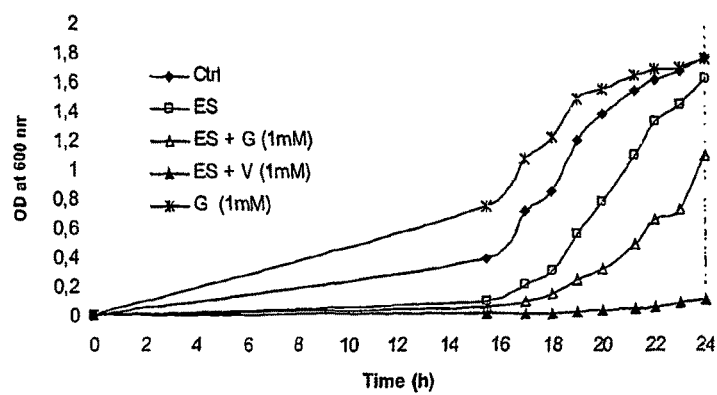
FIG. 9 shows the growth retardation of *Candida albicans* in the presence of oxidase/peroxidase, substrate+halide (ES), guaiacol (G), oxidase/peroxidase, substrate+halide with guaiacol (ES+G), oxidase/peroxidase, substrate+halide with vanillin (ES+V) according to an embodiment of the present invention. Medium without oxidase/peroxidase are used as reference (Ctrl).

A yeast cell culture (A600=0.05) was grown in Sabouraud Dextrose (SD) broth (Difco™, Becton Dickinson) in the presence of a 0.02% dilution (suboptimal concentration) of the enzyme/substrate system described in example 1. The addition of either guaiacol or vanillin shows that that an additional suppression of the fungal growth is obtained for at least 24 hours (see FIG. 9). The present example clearly shows a beneficial effect of adding enhancing agents of the present invention to antifungal oxidase/peroxidase compositions.

Example 6

Cell Toxicity on Mammalian Cells of Oxidase/Peroxidase Compositions Supplemented with Enhancers HaCat keratinocytes cells and mouse 3T3 fibroblast cells were grown in the following growth medium: DMEM medium (high glucose; Sigma) supplemented with heat inactivated calf serum (10%) (Life Technologies), L-glutamine (4 mM) (Sigma) and Streptomycin/Penicillin (100 U) (Sigma).

An alginate gel was prepared in water using 5% (w/v) Kelset (Keyser & MacKay), 0.5% (w/v) alginic acid, 28% (w/v) PEG 400, 1.5% (v/v) substrate (50% (w/v) glucose/ 1.4% (w/v) KI), 0.075% (v/v) glucose oxidase/lactoperoxidase solution and 200 µM guaiacol. As a control an identical gel without guaiacol was prepared.

One gram of the alginate gel was dissolved in 9 ml growth medium (diluted alginate gel).

Cells were seeded at subconfluency. After overnight incubation at 37° C., 5% $CO_2$, growth medium was replaced by diluted alginate gel and the cells were incubated at 37° C., 5% $CO_2$ for another 24 hours. Medium was decanted and 100 µl fresh growth medium containing 0.5 mg/ml MTT (1-(4,5-Dimethylthiazol-2-yl)-3,5-diphenylformazan) was added to the cells. Cells were incubated in this MTT-medium for an additional 3 h. Cell viability and metabolism was assayed by determining the chromophoric conversion product of MMT at 570 nm.

Figure 10:
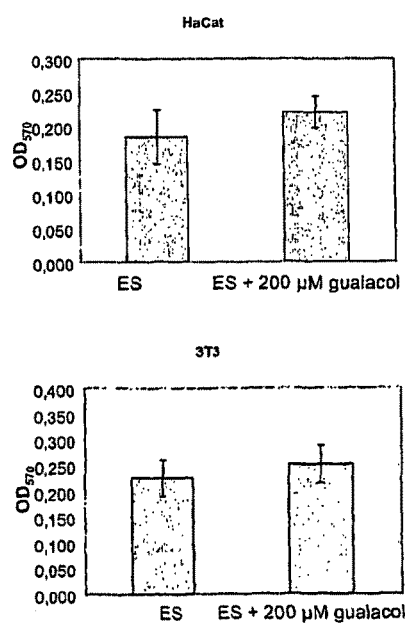
FIG. 10 shows the cell toxicity of oxidase/peroxidase+substrate+halide (ES) with and without guaiacol on mammalian cells (top panel: HaCat keratinocytes, bottom panel 3T3 fibroblast cells) according to an embodiment of the present invention.

FIG. 10 shows that there is no statistical difference (HaCaT: p=0.31; 3T3: p=0.32; t-test) in metabolic activity of cells incubated in the alginate hydrogel with or without guaiacol. The control conditions (ES only) have been published in Vandenbulcke et al. (2006) *Int J Low Extrem Wounds.* 5, 109-114. The present example shows that the addition of the enhancer guaiacol has no detrimental effect on the viability of mammalian cells.

Example 7

Antimicrobial Effect of Hydrogels with Oxidase/Peroxidase and Enhancers

An alginate gel was prepared in water using 5% (w/v) Kelset (Keyser & MacKay), 0.5% (w/v) alginic acid, 28% (w/v) PEG 400, 1.5% (v/v) substrate (50% glucose/1.4% KI), 0.075% (v/v) glucose oxidase/lactoperoxidase solution and 5 mM guaiacol. As a control an identical gel without guaiacol was prepared.

Bacteria (Gram-negative *E. coli* and Gram-positive *S. aureus*) were incubated in the above gel using 1 g gel, 100 µl of a 0.25% (v/v) ES solution, 100 µl bacterial suspension ($A_{600}$=0.25) and 300 µl water.

Figure 11:
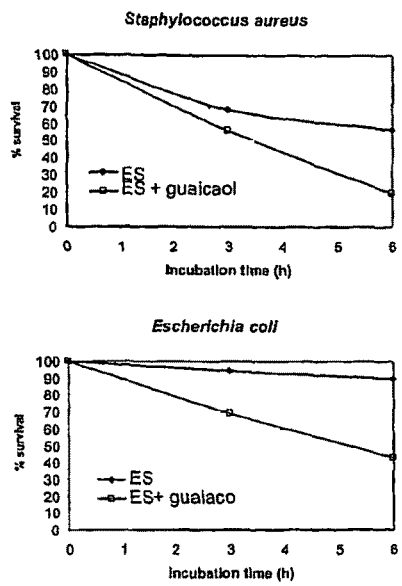
FIG. 11 shows the antibacterial effect of oxidase/peroxidase, substrate+halide (ES), with and without guaiacol on gram-positive and gram-negative bacteria according to an embodiment of the present invention.
Figure 12:
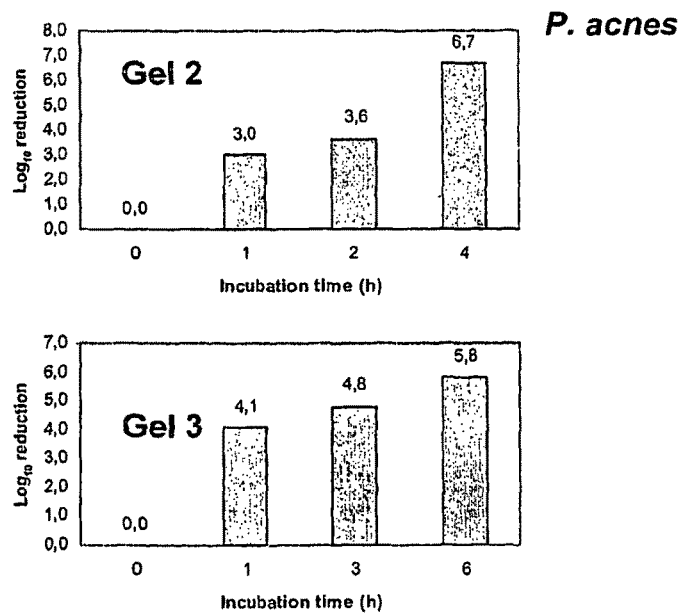
FIG. 12 shows the antibacterial effect of a hydrogel formulation with oxidase/peroxidase+substrate (+halide), and guaiacol or guaiacol+vanillin on anaerobic bacteria according to an embodiment of the present invention. Hydrogel compositions are described in table 3.
Figure 13:
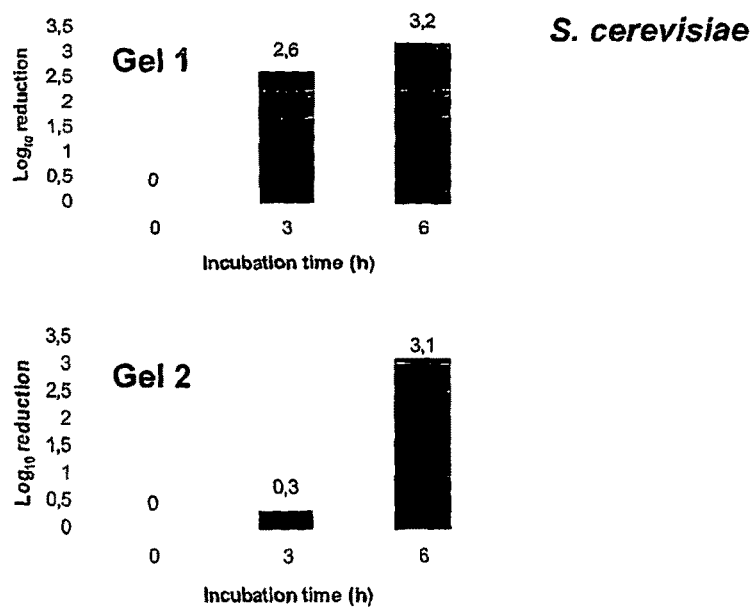
FIG. 13 shows the antifungal effect of a hydrogel formulation with oxidase/peroxidase+substrate (+halide), and guaiacol according to an embodiment of the present invention. Hydrogel compositions are described in table 3.
Figure 14:
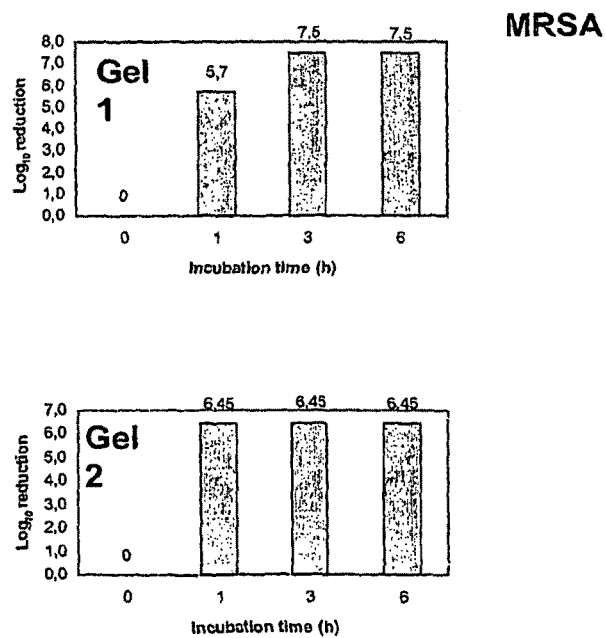
FIG. 14 shows the antibacterial effect of a hydrogel formulation with oxidase/peroxidase+substrate+halide, and guaiacol or guaicol+vanillin on aerobic bacteria according to an embodiment of the present invention. Hydrogel compositions are described in table 3.

Samples were taken at different time points and plated on Tryptic Soy Agar plates. FIG. 11 shows that the gel with oxidase/peroxidase and enhancing agent is both effective on gram-positive and gram-negative bacteria.

Example 8

Antimicrobial Effect of Hydrogel Formulations with Oxidase/Peroxidase and Enhancing Agents Different gel compositions (described in table 3) were assayed for their antimicrobial effect on the following microorganisms: *Staphylococcus aureus* methicillin-resistant (MRSA) bacteria; *Propionibacterium acnes* bacteria and *Saccharomyces cerevisiae* yeast.

TABLE 3 compositions of gels with oxidase/peroxidase and enhancing agents.

| gel 1 | gel 2 | gel 3 |
| --- | --- | --- |
| 5% (w/v) Kelset (Keyser & MacKay) | 1.5% (w/v) Pemulen (Noveon) [polyacrylic acid] | 1.5% (w/v) Pemulen (Noveon) [polyacrylic acid] |
| 0.5% (w/v) alginic acid | 1% (w/v) arginine | 1% (w/v) arginine |
| 28% (w/v) PEG 400 | 10% (w/v) PEG400 | 10%(w/v) PEG400 |
| 1.5% (v/v) substrate (50% (w/v) glucose/1.4% (w/v) KI) equals 0.75% (w/v) glucose + 0.021% (w/v) KI | 1.5% (v/v) substrate (50% (w/v) glucose/1.4% (w/v) KI) equals 0.75% (w/v) glucose + 0.021% (w/v) KI | 3% (v/v) substrate (50% glucose/1.4% (w/v) KI) equals 1.5% (w/v) glucose + 0.042% (w/v) KI |
| 0.075% (v/v) enzyme mix (glucose oxidase/lactoperoxidase) equals 1.15 U/ml glucose oxidase + 1.5 U/ml lactoperoxidase | 0.075% (v/v) enzyme mix (glucose oxidase/lactoperoxidase) equals 1.15 U/ml glucose oxidase + 1.5 U/ml lactoperoxidase | 0.15% (v/v) enzyme mix (glucose oxidase/lactoperoxidase) equals 2.3 U/ml glucose oxidase + 3 U/ml lactoperoxidase |
| 200 µM guaiacol | 20 µM guaiacol | 50 µM guaiacol/200 µM vanillin |
| $dH_2O$ add 100% | $dH_2O$ add 100% | $dH_2O$ add 100% |

100 µl of bacterial cells or 0.5 ml of *S. cerevisiae* cells ($OD_{600}$ of approximately 1), were mixed with 5 g gel. The mixture was incubated for 6 hours at 37° C. for bacteria and at 30° C. for *S. cerevisiae*.

To determine the number of surviving microorganisms, dilutions were made at the indicated timepoints in ($10^{-1}$, $10^{-3}$ and $10^{-5}$ dilutions for bacteria and $10^{-1}$, $10^{-2}$ and $10^{-3}$ dilutions for *S. cerevisiae*). Subsequently, 100 µl of the dilutions were plated on Tryptic Soy Agar (TSA) plates for MRSA, on fastidious anaerobe agar (ANA) plates for *P. acnes* or on Sabouraud Dextrose Agar (SDA) plates for *S. cerevisiae*. Plates were incubated for 24 hours at 37° C. (bacteria) or 30° C. (*S. cerevisiae*) for 24-48 hours and colony-forming units were counted.

For the anaerobic bacteria *Propionibacterium acnes*, incubation of the gel with the bacteria as well as growth on the ANA plates was performed in anaerobic jars (10% $CO_2$, 5% $H_2$ and 85% $N_2$). The anaerobic environment was created using an Anoxomat™ device (Mart® Microbiology BV, The Netherlands).

The data presented show that, with the gel compositions of table 3, that enhancers from 20 µM onwards reduce the bacterial growth about 1000 times. In order to reduce the growth of yeast to a similar extent, higher concentrations of enhancer are needed.

Example 9

Animal Model for the Assaying the Effect of Enhancing Agents

The effect of the enhancing agents on the reduction of wound infection and on wound healing is examined in mice. The mice are anaesthetised and their backs are shaved. Full-thickness wounds are applied on the shaved backs of the mice.

To verify the effect of the enhancing agents on the reduction of infection in these wounds, 100 µl of a *Staphylococcus aureus* suspension is applied on the full-thickness wound and this infected wound is covered with a hydrogel containing standard concentrations of oxidase/peroxidase enzyme system and varying concentrations of enhancing agent. Control conditions are infected full-thickness wounds covered with a hydrogel containing the oxidase/peroxidase enzyme system but lacking the enhancing agent. The rate of reduction of infection is monitored in time.

To verify the effect of the enhancing agents on wound healing, a hydrogel containing the oxidase/peroxidase enzyme system and the enhancing agent is applied to full-thickness wounds on the back of mice and the healing process is monitored in time until full closure of the wound. In control conditions the full-thickness wounds are covered with a hydrogel containing the oxidase/peroxidase enzyme system but lacking the enhancing agent.

Example 10

Comparative Study of Oxidase/Peroxidase Compositions with Enhancers on Chronic Leg Ulcers Gel formulations of oxidase/peroxidase compositions supplemented with enhancing agents as described in table 3 of example are used in the treatment of chronic leg ulcers as described in de la Brassinne et al (2006) *J. Eur. Acad. Dermatol. Venereol.* 20, 131-135.

Different patient groups are treated for a period of 28 days. Both the surface (acetate tracing and planimetry) and the volume (Jeltrate mould impression and weighting) of each wound were measured at baseline and after 7, 14 and 28 days of treatment.

Control groups are treated with a gel comprising oxidase/peroxidase and substrate but no enhancing agent.

It is observed that the compositions comprising enhancing agent effectively demonstrate anti-microbial activity, with limited toxic effects. The compositions are well-tolerated up to the end of the treatment period.

The invention claimed is:

1. An antimicrobial composition in the form of a hydrogel comprising a combination of
    glucose and glucose oxidase,
    one or more peroxidases,
    from 0.01 to 0.1% of water-soluble iodide salt by weight,
    from 1 to 50 mg/100 g of one or more enhancing agents selected from the group consisting of a benzene molecule substituted with a —OH or —$(CH_2)_n$OH (n=1, 2, 3, or 4) group and substituted with one alkoxy group with a chain length of 1, 2, 3 or 4 carbon atoms and further optionally substituted with one to 4 substituents, each independently selected from the group consisting of an hydroxy group, an aldehyde, a ketone, an acid and a halogen, an hydroxyalkyl group with 1, 2, 3 or 4 carbon atoms, a linear or branched alkyl group or a linear or branched alkenyl group with 1, 2, 3 or 4 carbon atoms, wherein said hydroxyalkyl, alkyl or alkenyl groups are further optionally substituted with a halogen, carboxyl, hydroxyl, aldehyde or ketone group, and
wherein the hydrogel comprises alginate and water
    suitable for dissolving the one or more peroxidases, the one or more enhancing agents, and the iodide,
wherein said composition is formulated for prolonged use on skin.

2. The composition of claim 1, further comprising one or more pseudohalides.

3. The composition according to claim 1, wherein said benzene molecule is a lipophilic molecule with an octanol/water partition coefficient X log P between 1 and 4.

4. The composition according to claim 1, wherein the —OH or —$(CH_2)_n$OH (n=1, 2, 3, or 4) group and the alkoxy group on the benzene molecule are in ortho position.

5. The composition according to claim 4, wherein the benzene molecule has a general structure represented by formula (I)

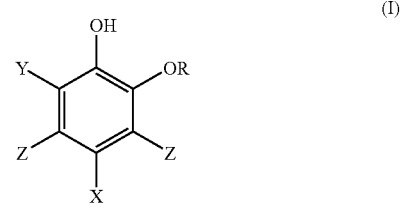

wherein R is —$CH_3$ or —$CH_2CH_3$, wherein X is selected from the group consisting of —H, —CHO, —COOH and —$COCH_3$, wherein Y is selected from the group consisting of —H, a halogen and an alkyl group with a chain length of 1, 2, 3 or 4 carbon atoms, and wherein both positions Z are independently selected from the group consisting of —H and an alkyl group with a chain length of 1, 2, 3 or 4 carbon atoms.

6. The composition according to claim 1, wherein said benzene molecule is selected from the group consisting of an hydroxyalkyl-alkoxybenzene, an alkoxyphenol, an hydroxyalkyl alkoxybenzaldehyde, and a hydroxy alkoxybenzaldehyde.

7. The composition according to claim 1, wherein said benzene molecule is a methoxyphenol.

8. The composition according to claim 1, wherein said benzene molecule is guaiacol.

9. The composition according to claim 5, wherein said benzene molecule is a hydroxymethoxybenzaldehyde.

10. The composition according to claim 5, wherein said benzene molecule is vanillin.

11. The composition according to claim 2, wherein the composition further excludes thiocyanate ions.

12. The composition according to claim 1, wherein said composition is a pharmaceutical composition.

13. The composition according to claim 1, wherein said composition is formulated for topical application.

14. A wound dressing comprising the composition of claim 1.

15. The composition of claim 1, wherein said peroxidase is a lactoperoxidase.

16. The composition of claim 1, wherein said peroxidase is a myeloperoxidase.

17. The composition according to claim 1, wherein said iodide salt is KI.

18. The composition of claim 1, wherein said alginate is sodium alginate.

19. The composition of claim 1, wherein the prolonged use on the skin is for a period in the range of 2 to 24 hours.

20. The composition of claim 1, wherein the prolonged use on the skin is for a period between 2 and 8 hours.

21. An antimicrobial composition in the form of a hydrogel comprising a combination of
glucose and glucose oxidase,
one or more peroxidases,
from 0.01 to 0.1% of water-soluble iodide salt by weight,
from about 10 to 400 µM of one or more enhancing agents selected from the group consisting of a benzene molecule substituted with a —OH or —(CH$_2$)$_n$OH (n=1, 2, 3, or 4) group and substituted with one alkoxy group with a chain length of 1, 2, 3 or 4 carbon atoms and further optionally substituted with one to 4 substituents, each independently selected from the group consisting of an hydroxy group, an aldehyde, a ketone, an acid and a halogen, an hydroxyalkyl group with 1, 2, 3 or 4 carbon atoms, a linear or branched alkyl group or a linear or branched alkenyl group with 1, 2, 3 or 4 carbon atoms, wherein said hydroxyalkyl, alkyl or alkenyl groups are further optionally substituted with a halogen, carboxyl, hydroxyl, aldehyde or ketone group, and
wherein the components to form a hydrogel are an alginate and water
suitable for dissolving the one or more peroxidases, the one or more enhancing agents, and the iodide,
wherein said composition is formulated for prolonged use on skin.

22. A method of treating a microbial infection on the animal or human skin, hair or nails, comprising the step of contacting said skin, hair or nails with a composition comprising a combination comprising:
glucose and glucose oxidase,
one or more peroxidases,
from 0.01 to 0.1% of water-soluble iodide salt by weight,
from 1 to 50 mg/100 g of one or more enhancing agents selected from the group consisting of a benzene molecule substituted with a —OH or (CH$_2$)$_n$OH (n=1, 2, 3 or 4) group and substituted with one alkoxy group with a chain length of 1, 2, 3 or 4 carbon atoms and further optionally substituted with one to 4 substituents, each independently selected from the group consisting of an hydroxy group, an aldehyde, a ketone, an acid and a halogen, an hydroxyalkyl group with 1, 2, 3 or 4 carbon atoms, a linear or branched alkyl group or a linear or branched alkenyl group with 1, 2, 3 or 4 carbon atoms, wherein said hydroxyalkyl, alkyl or alkenyl groups are further optionally substituted with a halogen, carboxyl, hydroxyl, aldehyde or ketone group,
wherein the composition is in the form of a hydrogel comprising alginate and water, thereby treating said microbial infection.

23. The method according to claim 22, which further comprises the step of maintaining the composition on said skin, hair and/or nails for a time period between 2 and 8 hours.

24. The method according to claim 22, wherein the treatment is performed on a wound or a burn.

25. The method according to claim 22, wherein said substituted benzene molecule is selected from the group consisting of an hydroxyalkyl-alkoxybenzene, an alkoxyphenol, an hydroxyalkyl alkoxybenzaldehyde or a hydroxy alkoxybenzaldehyde.

26. The method according to claim 22, wherein the substituted benzene molecule has a general structure represented by formula (I)

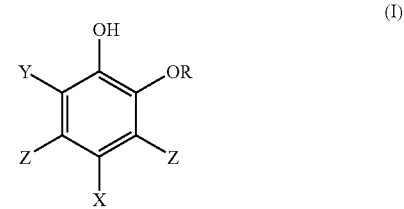

wherein R is —CH$_3$ or —CH$_2$CH$_3$, wherein X is selected from the group consisting of —H, —CHO and —COCH$_3$, wherein Y is selected from the group consisting of —H, a halogen and an alkyl group with a chain length of 1, 2, 3 or 4 carbon atoms, and wherein both positions Z are independently selected from the group consisting of —H and an alkyl group with a chain length of 1, 2, 3 or 4 carbon atoms.

27. The method according to claim 25, wherein said benzene molecule is a methoxyphenol.

28. The method according to claim 27, wherein said benzene molecule is guaiacol.

29. The method according to claim 25, wherein said benzene molecule is a hydroxymethoxybenzaldehyde.

30. The method according to claim 29, wherein said benzene molecule is vanillin.

31. The method according to claim 22, wherein said composition further comprises one or more pseudo-halides.

32. The method according to claim 22, wherein the composition comprises no thiocyanate ions.

33. A method of treating a microbial infection on the animal or human skin, hair or nails, comprising the step of contacting said skin, hair or nails with a composition comprising a combination comprising:
glucose and glucose oxidase,
one or more peroxidases,
from 0.01 to 0.1% of water-soluble iodide salt by weight,
from about 10 to 400 µM of one or more enhancing agents selected from the group consisting of a benzene molecule substituted with a —OH or (CH$_2$)$_n$OH (n=1, 2, 3 or 4) group and substituted with one alkoxy group with a chain length of 1, 2, 3 or 4 carbon atoms and further optionally substituted with one to 4 substituents, each independently selected from the group consisting of an hydroxy group, an aldehyde, a ketone, an acid and a halogen, an hydroxyalkyl group with 1, 2, 3 or 4 carbon atoms, a linear or branched alkyl group or a linear or branched alkenyl group with 1, 2, 3 or 4 carbon atoms, wherein said hydroxyalkyl, alkyl or alkenyl groups are further optionally substituted with a halogen, carboxyl, hydroxyl, aldehyde or ketone group, wherein the composition is in the form of a hydrogel comprising alginate and water, thereby treating said microbial infection.

* * * * *